US010898657B2

(12) United States Patent
Jaouen et al.

(10) Patent No.: US 10,898,657 B2
(45) Date of Patent: Jan. 26, 2021

(54) MANUAL INJECTION DEVICE

(71) Applicant: APTAR FRANCE SAS, Le Neubourg (FR)

(72) Inventors: Quentin Jaouen, Gournay en Bray (FR); Anthony Saussaye, Louviers (FR)

(73) Assignee: APTAR FRANCE SAS, Le Neubourg (FR)

( * ) Notice: Subject to any disclaimer, the term of this patent is extended or adjusted under 35 U.S.C. 154(b) by 86 days.

(21) Appl. No.: 16/339,196

(22) PCT Filed: Oct. 2, 2017

(86) PCT No.: PCT/FR2017/052698
§ 371 (c)(1),
(2) Date: Apr. 3, 2019

(87) PCT Pub. No.: WO2018/065714
PCT Pub. Date: Apr. 12, 2018

(65) Prior Publication Data
US 2019/0240422 A1 Aug. 8, 2019

(30) Foreign Application Priority Data
Oct. 4, 2016 (FR) ...................................... 16 59549

(51) Int. Cl.
*A61M 5/32* (2006.01)
*A61M 5/31* (2006.01)
(52) U.S. Cl.
CPC ........ *A61M 5/3287* (2013.01); *A61M 5/3129* (2013.01); *A61M 5/326* (2013.01); *A61M 2005/3267* (2013.01)
(58) Field of Classification Search
CPC ........ A61M 2005/2073; A61M 5/3287; A61M 5/3129; A61M 5/326; A61M 2005/3267;
(Continued)

(56) References Cited

U.S. PATENT DOCUMENTS

| 5,320,609 A | 6/1994 | Haber et al. |
| 2016/0303323 A1 | 10/2016 | Saussaye et al. |

FOREIGN PATENT DOCUMENTS

| EP | 2 572 741 A1 | 3/2013 |
| FR | 2 884 722 A1 | 10/2006 |

(Continued)

OTHER PUBLICATIONS

International Search Report of PCT/FR2017/052698 dated Dec. 1, 2017.

(Continued)

*Primary Examiner* — Amber R Stiles
*Assistant Examiner* — Sarah Zagorin
(74) *Attorney, Agent, or Firm* — Sughrue Mion, PLLC

(57) ABSTRACT

A manual injection device having a lower body and a fluid reservoir that moves axially in the lower body. The reservoir includes a piston and needle; an upper body mounted to move axially relative to the lower body, the upper body including a piston rod co-operating with the piston; and a sleeve mounted to move relative to the lower body between a rest position and a projecting position. The sleeve is blocked in its rest position before the injection device is actuated, and urged automatically into its projecting position after injection. The piston rod co-operates with the reservoir to form an injection lock, the force for moving the reservoir axially being less than the force for triggering the injection lock, such that pricking is performed before injection. Before actuation, the piston rod is connected to a ring that is fastened on a radial collar of the reservoir.

5 Claims, 3 Drawing Sheets

(58) Field of Classification Search
CPC ............ A61M 5/50; A61M 2005/5073; A61M 2005/5006; A61M 5/315; A61M 5/31511; A61M 5/31501; A61M 5/31505; A61M 5/5013; A61M 5/502; A61M 2005/31506; A61M 2005/31508
See application file for complete search history.

(56) References Cited

FOREIGN PATENT DOCUMENTS

| | | | |
|---|---|---|---|
| FR | 3 019 748 A1 | 10/2015 | |
| WO | 2006/129196 A1 | 12/2006 | |
| WO | 2012/045350 A1 | 4/2012 | |
| WO | WO-2012045350 A1 * | 4/2012 | .......... A61M 5/2033 |
| WO | 2014/053378 A2 | 4/2014 | |
| WO | 2014/150201 A1 | 9/2014 | |

OTHER PUBLICATIONS

International Preliminary Report on Patentability dated Mar. 5, 2019 in International Application No. PCT/FR2017/052698.

\* cited by examiner

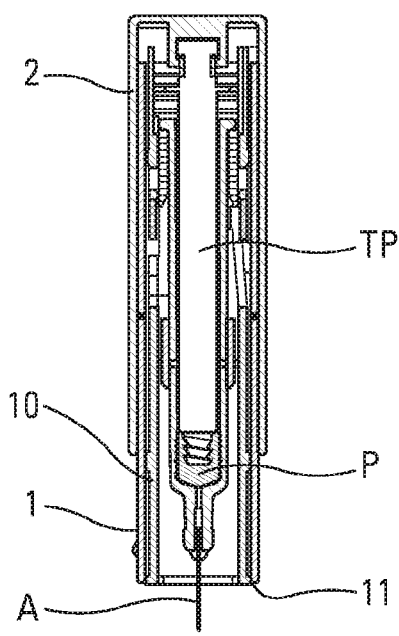
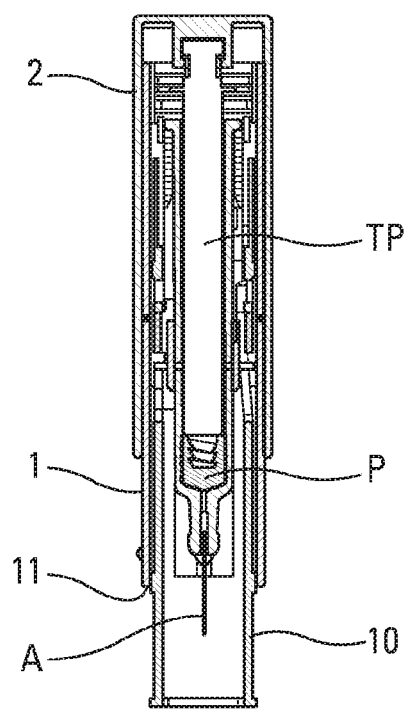
Fig. 5
Fig. 6
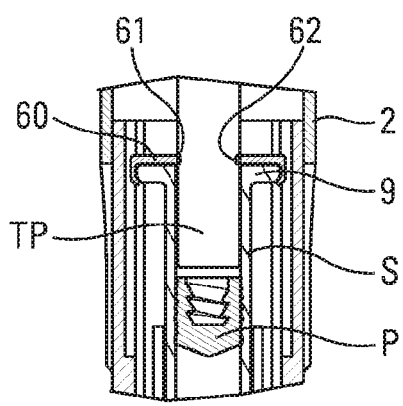
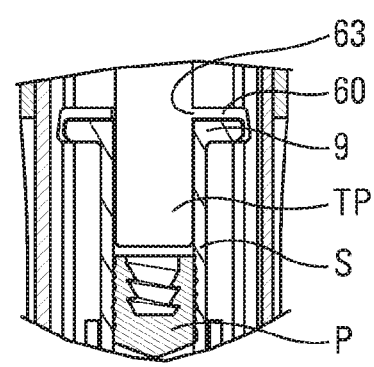
Fig. 7
Fig. 8
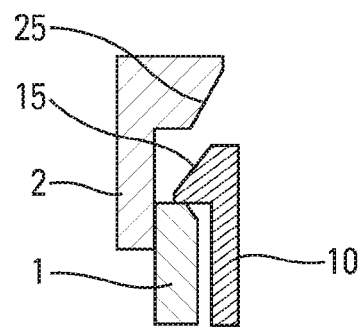
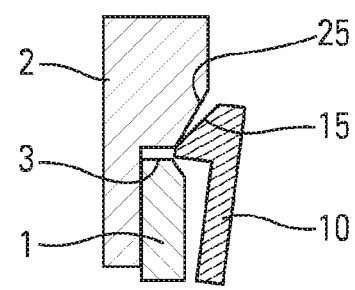
Fig. 9
Fig. 10

MANUAL INJECTION DEVICE

CROSS REFERENCE TO RELATED APPLICATIONS

This application is a National Stage of International Application No. PCT/FR2017/052698 filed Oct. 2, 2017, claiming priority based on French Patent Application No. 1659549 filed Oct. 4, 2016.

The present invention relates to a manual injection device.

The purpose of manual injection devices is mainly to cause the needle to penetrate into the patient's body, and also to protect the needle of the syringe before, during, and after injection. In contrast, the actual injection of the fluid contained in the syringe into the patient's body is done manually by the user. Manual injection devices are relatively complex devices that must satisfy a certain number of constraint requirements in order to be reliable. The robustness of the device, its handling, and its ease of use for the user are also important elements. In addition, since most manual injection devices are for single use, the cost of manufacture and of assembly is also a factor that needs to be taken into account.

Numerous manual injection devices exist on the market, but they all present a certain number of drawbacks.

Thus, use of the manual injection device must not be too difficult, as this would prevent weak people from using it. It is also necessary to avoid injection beginning before the needle has penetrated into the patient's body. Furthermore, in order to avoid any risk of injury before and after using the device, the manual injection device should include a needle safety device that avoids the needle being visible before and after the device is used. Obviously, the safety device should also be reliable and not be released too easily. It should also be functional even when the user actuates the manual injection device poorly, e.g. when the user removes it too soon from the body, before the end of injection.

Documents WO 2014/150201, WO 2011/047298, WO 2012/045350, WO 2006/129196, WO 2006/111862, FR 2 884 722, U.S. Pat. No. 5,320,609, EP 2 572 741, and FR 3 019 748 describe prior-art devices.

An object of the present invention is to provide a manual injection device that does not have the above-mentioned drawbacks, and that makes it possible to satisfy the various major requirements and constraints for safe and reliable use of the manual injection device.

In particular, an object of the present invention is to provide a manual injection device that avoids the risk of fluid injection beginning before the needle has penetrated fully into the injection site.

Another object of the present invention is to provide a manual injection device that is reliable in use, that is safe and that prevents any risk of injury, and that is simple and inexpensive to manufacture, to assemble, and to use.

The present invention thus provides a manual injection device comprising:
- a lower body that receives a reservoir, said reservoir being mounted to move axially in said lower body and containing fluid to be injected, said reservoir including a piston and a needle;
- an upper body that is mounted to move axially relative to said lower body during actuation, said upper body including a piston rod that co-operates with said piston during injection so as to move it in the reservoir; and
- a sleeve that is mounted to move relative to said lower body between a rest position, in which said sleeve is arranged inside said lower body, and a projecting position, in which said sleeve is moved axially out of said lower body, said sleeve being blocked in its rest position before the manual injection device is actuated, and being urged automatically into its projecting position after injection;
- said piston rod co-operating with said reservoir, or with any element that is secured to said reservoir, so as to form an injection lock, the force necessary for moving said reservoir axially in said lower body being less than the force necessary for triggering said injection lock, such that said pricking is performed before said injection;

wherein, before actuation, said piston rod is connected to a ring that is fastened, in particular crimped, on a radial collar of said reservoir.

Advantageously, before actuation, said piston rod is connected via breakable bridges to said ring.

In a variant, said ring includes a radially-inner projection that, before actuation, co-operates with a groove of said piston rod.

Advantageously, said sleeve includes an end that is elastically deformable in a radially-inward direction, said end, in its rest position, bearing against a radial shoulder of the lower body, said upper body co-operating, at the end of injection, via a cam, with said end of said sleeve, so as to deform said end in a radially-inward direction.

These and other characteristics and advantages of the present invention appear more clearly from the following detailed description, given by way of non-limiting examples, and with reference to the accompanying drawings, and in which:

FIG. 5 is a view similar to the view in FIG. 4, at the end of injection;

FIG. 6 is a view similar to the view in FIG. 5, after the post-injection safety device has been triggered;

FIG. 7 is a view of a detail of a first variant embodiment of the injection lock;

FIG. 8 is a view of a detail of a second variant embodiment of the injection lock; and FIGS. 9 and 10 are diagrammatic views of a detail of the triggering of the post-injection safety device;

The manual injection device shown in the figures comprises a lower body 1 and an upper body 2 that is movable axially relative to said lower body 1 during actuation. It should be observed that the lower body 1 and the upper body 2 may each be made as a single piece or else out of a plurality of assembled-together portions. In known manner, the lower body 1 contains a reservoir S containing the fluid to be injected, a needle A that is fastened to said reservoir S and through which the fluid is dispensed, and a piston P that is adapted to move in said reservoir S so as to perform the injection. The upper body 2 includes a piston rod TP that co-operates with said piston P during injection so as to move it in the reservoir S. Before use, the needle A may be protected by a protective cap. Typically, the reservoir S may be a conventional pre-filled syringe, provided with a radial collar 9. Said reservoir S is movable axially in said lower body 1 so as to perform pricking, then it is stationary relative to said lower body 1 during injection. Said piston rod TP is stationary relative to said upper body 2. Thus, when the upper body 2 slides axially relative to the lower body 1, the piston rod TP slides axially relative to the reservoir S.

Before actuation, a post-injection safety sleeve 10 is arranged inside the lower body. After injection, said sleeve 10 is moved axially out of the lower body 1 into a projecting position in which it is arranged around the needle A, so as to avoid any risk of injury with said needle A, thereby forming a post-injection safety device. The sleeve 10 is advantageously urged towards its projecting position by a spring that may be of any type. Before actuation, said sleeve 10 is blocked and prevented from moving towards its projecting position by blocking means that are released at the end of injection.

The piston rod TP co-operates with the reservoir S (or with any element that is secured to said reservoir S, such as, for example, a reservoir support or a ring that is snap-fastened on said reservoir), so as to define an actuation lock. The lock comprises a pricking lock and an injection lock.

In the invention, the pricking lock is actuated before the injection lock, i.e. the axial force necessary for moving the reservoir S axially in the lower body 1 is less than the axial force necessary for triggering the injection lock. Thus, when the user presses the device against the injection site and presses axially on the upper body 2 so as to cause it to slide axially relative to the lower body 1, the reservoir S initially moves axially inside the lower body 1 so as to perform pricking. The piston rod TP moves axially inside the reservoir S only after pricking has terminated.

Figure 1:
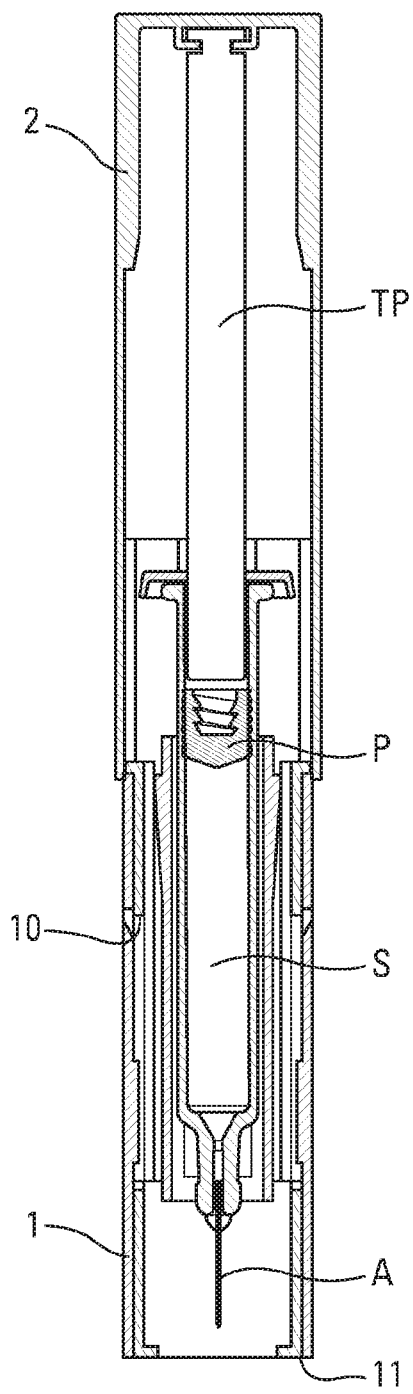
FIG. 1 is a diagrammatic section view of a manual injection device in an advantageous embodiment, in its rest position, before pricking.
Figure 2:
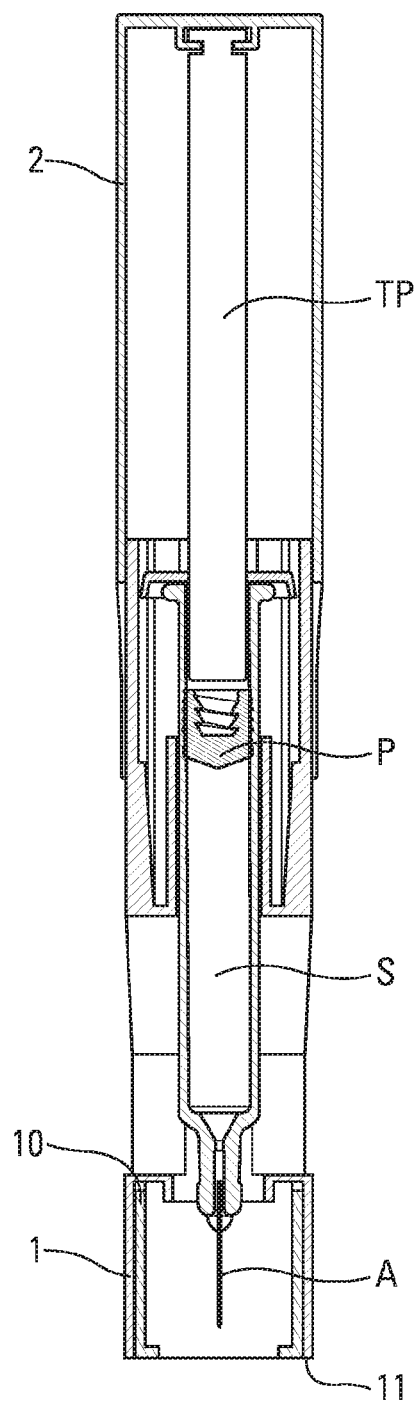
FIG. 2 is a view similar to the view in FIG. 1 from another view point.
Figure 3:
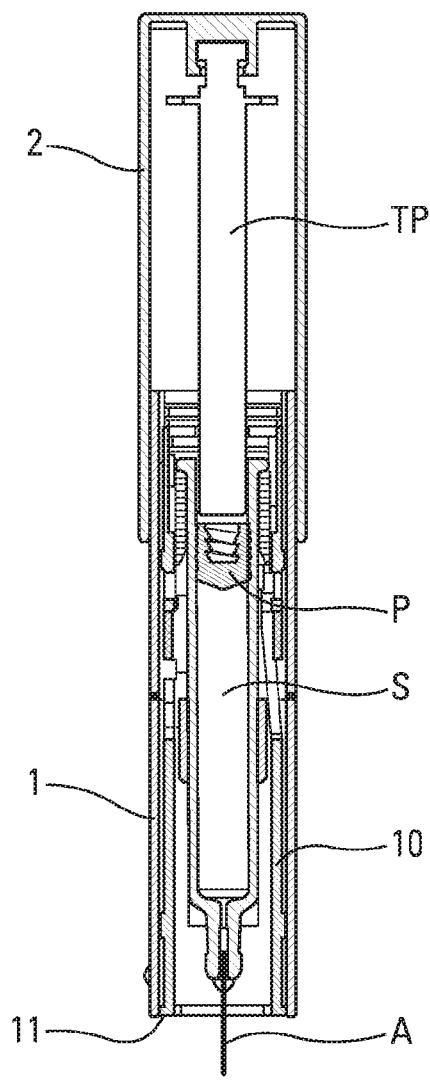
FIG. 3 is a view similar to the view in FIG. 2, at the end of pricking, before the injection lock is triggered.
Figure 4:
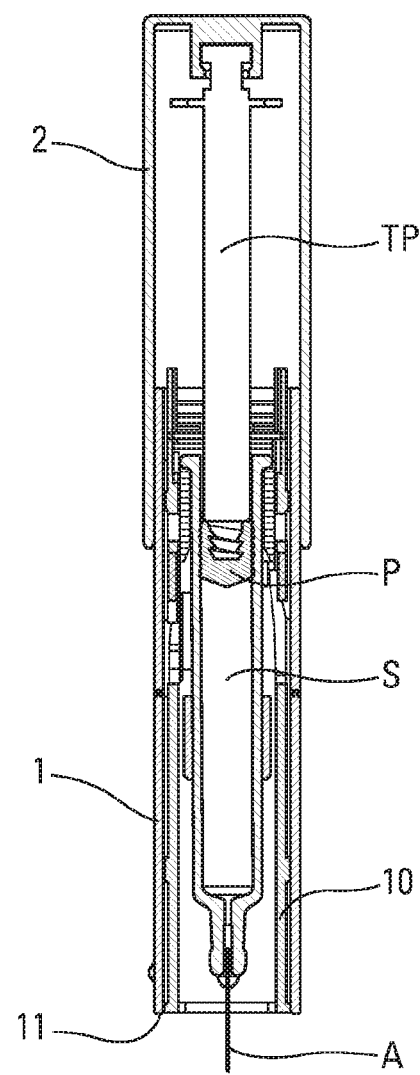
FIG. 4 is a view similar to the view in FIG. 3, after the injection lock has been triggered.

FIGS. 1 to 6 show an advantageous embodiment and show various positions in the actuation sequence of the manual injection device.

With reference to FIGS. 1 to 6, the user presses the bottom end 11 of the lower body 1 around the injection site, and exerts axial pressure on the upper body 2. Since the resistance to the injection lock triggering, as described below, is greater than the resistance to the axial movement of the reservoir S in said lower body 1, it is the reservoir S that initially slides axially into the lower body 1. This enables the needle A to penetrate into the injection site under the effect of said axial pressure from the user. It is only when the reservoir S reaches its pricked position, in axial abutment in the lower body 1, thereby preventing any additional axial movement of said reservoir S, that the actuation force or axial pressure of the user serves to trigger the injection lock. After triggering said injection lock, the upper body 2, and thus also the piston rod TP, move axially relative to the reservoir S, so as to move the piston P in the reservoir S and thus inject the fluid contained in the reservoir through the needle A and into the injection site. At the end of injection, when the user removes the manual injection device from the injection site, the sleeve 10 is released from the blocking means and moves automatically, e.g. under the effect of a return spring, to its second projecting position in which it is locked, so as to avoid any risk of injury with the needle A, as can be seen in FIG. 6.

FIG. 8 shows a first variant embodiment of the injection lock. In this variant, the injection lock is formed between the piston rod TP and a ring 60 that is fastened, in particular crimped, directly on the radial collar 9 of the syringe S. Said ring 60 includes a radially-inner projection 61 that is fastened to said piston rod TP via breakable bridges 63. The resistance of the breakable bridges 63 against breaking is greater than the force for triggering the pricking lock, i.e. for moving the reservoir S axially in the lower body 1, such that pricking takes place before injection.

FIG. 7 shows another variant in which, before actuation, said radially-inner projection 61 of the crimping ring 60 co-operates with a groove 62 of the piston rod TP. The force necessary for disengaging said projection 61 from said groove 62 is greater than the force for triggering the pricking lock, i.e. for moving the reservoir S axially in the lower body 1, such that pricking takes place before injection.

Other variants of the pricking lock and/or of the injection lock may also be envisaged.

FIGS. 9 and 10 show the triggering of the post-injection safety device, with the sleeve 10 moving out of the lower body 1 towards its projecting position. The sleeve 10 includes an end 15 that is elastically deformable in a radially-inward direction. In the rest position, shown in FIG. 9, the end 15 bears against a radial shoulder 3 of the lower body 1. The sleeve 10 is thus blocked against any axial movement towards its projecting position relative to said lower body 1. At the end of injection, the upper body 2 comes to co-operate, via a cam 25, with said end 15 of the sleeve, so as to deform it in a radially-inward direction, as can be seen in FIG. 10. The sleeve 10 is thus no longer blocked, and it can move towards its projecting position, e.g. under the effect of an appropriate spring.

Although the present invention is described above with reference to advantageous embodiments and variants, naturally various modifications can be applied thereto by the person skilled in the art, without going beyond the ambit of the present invention, as defined by the accompanying claims.

The invention claimed is:

1. A manual injection device comprising:
   a lower body that receives a reservoir, said reservoir being mounted to move axially in said lower body and containing fluid to be injected, said reservoir including a piston and a needle;
   an upper body that is mounted to move axially relative to said lower body during actuation, said upper body including a piston rod that co-operates with said piston during injection so as to move the piston in the reservoir; and
   a sleeve that is mounted to move relative to said lower body between a rest position, in which said sleeve is arranged inside said lower body, and a projecting position, in which said sleeve is moved axially out of said lower body, said sleeve being blocked in the rest position before the manual injection device is actuated, and being urged automatically into the projecting position after injection;
   the manual injection device being characterized in that, before actuation, said piston rod is connected to a ring that is fastened on a radial collar of said reservoir so as to form an injection lock, a force necessary for moving said reservoir axially in said lower body being less than a force necessary for triggering said injection lock, such that pricking is performed before said injection.

2. A manual injection device according to claim 1, wherein, before actuation, said piston rod is connected via breakable bridges to said ring.

3. A manual injection device according to claim 1, wherein said ring includes a radially-inner projection that, before actuation, co-operates with a groove of said piston rod.

4. A manual injection device according to claim 1, wherein said sleeve includes an end that is elastically deformable in a radially-inward direction, said end, in said end's rest position, bearing against a radial shoulder of the lower body, said upper body co-operating, at an end of injection, via a cam with said end of said sleeve, so as to deform said end in a radially-inward direction.

5. A manual injection device according to claim 1, wherein the ring is crimped on the radial collar.

* * * * *